(12) United States Patent
Alami et al.

(10) Patent No.: US 6,344,346 B1
(45) Date of Patent: Feb. 5, 2002

(54) POLYSACCHARIDE, MICRO-ORGANISM AND METHOD FOR OBTAINING SAME, COMPOSITION CONTAINING IT AND APPLICATION

(75) Inventors: Younes Alami; Thierry Heulin, both of Aix En Provence; Michel Milas, Herbeys; Régis De Baynast, Versailles; Alain Heyraud, Veurey-Voroize; Agnès Villain, Grenoble, all of (FR)

(73) Assignees: Agro Industrie Recherches et Developpement (ARD), Pomacle; Centre National de la Recherche Scientifique (CNRS), Paris, both of (FR)

( * ) Notice: Subject to any disclaimer, the term of this patent is extended or adjusted under 35 U.S.C. 154(b) by 0 days.

(21) Appl. No.: 09/355,921
(22) PCT Filed: Feb. 12, 1998
(86) PCT No.: PCT/FR98/00269
§ 371 Date: Feb. 22, 2000
§ 102(e) Date: Feb. 22, 2000
(87) PCT Pub. No.: WO98/35993
PCT Pub. Date: Aug. 20, 1998

(30) Foreign Application Priority Data

Feb. 12, 1997 (FR) .......................................... 97 01624

(51) Int. Cl.$^7$ ................................................. C12P 19/04
(52) U.S. Cl. .......................... 435/101; 435/72; 536/123
(58) Field of Search .................... 435/101, 72; 536/123

(56) References Cited

U.S. PATENT DOCUMENTS 5,455,343 A   10/1995   Fontaine et al. ......... 536/123.1

FOREIGN PATENT DOCUMENTS

| GB | 2 223 503 |   | 4/1990 |
| JP | 58-127701 | * | 7/1983 |
| JP | 02-092901 | * | 4/1990 |

OTHER PUBLICATIONS

Bernabé et al, Carb. Res. 279:339–352, 1995.*
Gidley et al, Carb. Res. 231:185–196, 1992.*
Gidley et al, Carb. Res. 160:381–396, 1987.*
Zevenhuizen et al, Carb. Res. 124:166–171, 1983.*

* cited by examiner

*Primary Examiner*—Francisco Prats

(57) ABSTRACT

The invention concerns a polysaccharide with a repeat unit having a lateral chain and comprising six neutral sugars among which glucose and galactose and an acid sugar, a solution greater than 0.2% by weight of said polysaccharide forming a transparent and elastic gel. The invention is applicable in the cosmetic, food, pharmaceutical and oil industries.

17 Claims, 5 Drawing Sheets

POLYSACCHARIDE, MICRO-ORGANISM AND METHOD FOR OBTAINING SAME, COMPOSITION CONTAINING IT AND APPLICATION

The invention relates to a novel polysaccharide, a micro-organism and method of obtaining it, a composition containing it and application thereof.

As is known, microbial populations constitute a wide reservoir for bringing new molecules into operation. Description of the bacteria in the rhizospheres of cereal plants was the first means of demonstrating the existence of nitrogen-fixing species, mostly associated with the roots of wheat, sunflower, rice and maize. In order to isolate these species, it was necessary to develop specific methods of isolation that is the "spermosphere model" for selecting the bacteria most adapted to the rhizosphere, and antibody trapping, using the specific antibodies of certain species. These bacteria are also involved in the mechanisms of attachment and colonisation of the roots.

For some years, research has concentrated on the capacity of most bacteria, present on the surface of roots and in the rhizosphere, to produce exopoly-saccharides (EPS). It has been amply demonstrated that these polymers play a part in colonisation of roots by bacteria and in aggregation of soil around the roots.

There has been recent work on the study of the capacity of strains to stimulate aggregation of soil around the roots of sunflower and wheat.

An aim of the invention is to provide a micro-organism which produces exopolysaccharides on a gelose medium, grows rapidly on culture medium requiring little in the way of agricultural raw materials (hydrolysed wheat bran, wheat peptides, glucose syrups, hydrolysed starch-factory co-products, for example), easy to use and of course non-pathogenic and genetically stable.

One strain discovered, for example, has a map and a gene sequence which codes for rRNA 16S, indicating that it belongs to the Rhizobiaceae family (the alpha sub-division of the proteobacteria). The percentage similarity to the nucleic acids of this region of the chromosome (rDNA 16S) of the strain YAS34 is 97.2% with Rhizobium etli and 96.2% with Rhizobium leguminosarum (strain LMG 9518). Hybridization on colonies of YAS34 with an oligonucleotide probe specific for Rhizobium (in the wide sense) in the nodD gene was found positive (personal communication from G. Laguerre, INRA, Dijon).

The presence of the nodD gene and the percentage similarity between the gene coding for rRNA 16S and species belonging to the Rhizobium genus are other factors indicating that the strain YAS34 is a Rhizobium.

The genotype imprint of the strain YAS34 by rep-PCR using three different primer sets (REP, ERIC and BOX) is available.

YAS 34 was deposited under number 1-1809 at the CNCM of the Institut Pasteur on Jan. 15, 1997.

The strain YAS 34 was isolated from the surface of the roots (rhizoplane) of a sunflower (Helianthus annuus cv Albena) taken in the four-leaf stage. The seeds used had not been treated with plant protectives and had been sterilised before sowing. The soil was alluvial, the main exchangeable cation being calcium.

The strain YAS 34 is a gram-negative, aerobic catalase-positive and oxidase-negative bacterium. It is a mobile rod bacterium which forms elastic, translucent, white colonies on an RCV-glucose medium (4 g/l).

The strain YAS 34 biosynthesises polysaccharide by fermentation in the presence of a culture medium containing a source of preferably assimilated carbon.

It has been shown that the most efficient carbonaceous sources in terms of growth and production of polysaccharides are glucose, fructose, saccharose and galactose.

This capacity to assimilate numerous glucides was a reason for studying the capacity of this strain to cause fermentation in various media of vegetable origin originating from fractionation of agricultural materials such as wheat, potato or grapes. Table I hereinafter shows the various media tested, and Table II shows the results obtained.

TABLE I

| AGRICULTURAL PRODUCTS | MEDIA TESTED | COMPOSITIONS SUGARS AND NITROGENOUS MATERIALS |
|---|---|---|
| Potato | JCII ED: electrodialysed clear juice II | |
| Wheat bran | JPAS: pressed juice after saccharification FAM: filtrate after micro-filtration | Glucose: 12–15 g/L Nitrogenous matter: 5.25 g/L |
| Grape | JRB 033 ED LD: pressed juice of grape marc after electrodialysis | Glucose: 10 g/L Fructose: 10 g/L Nitrogenous material: traces |

TABLE II

| NATURAL SUBSTRATES | $\mu$max (h-1) | OD at 600 nm max | VISCOSITY (cps at 25° C., 26 s-1) at 52 h | at 140 h | TOTAL CONSUM. OF GLUCOSE (g/L) |
|---|---|---|---|---|---|
| Potato | | | | | |
| JCII ED | 0.21 | 7.6 | 238 | 273 | 5.6 |
| JCII ED1/2 | 0.26 | 6.04 | 197 | 193 | 3.8 |
| Wheat bran | | | | | |
| JPAS 2/3 | 0.17 | 3.9 | 267 | 374 | 9.5 |
| FAM | 0.47 | 2.9 | 280 | 356 | 5.6 |
| Grape marc | | | | | |
| JRB 03 ED LD1/2 | nd | | 9 | 36 | 1.8 |

The medium called FAM, which originates from wheat bran and contains 12 g/L glucose and also 5.25 g/L nitrogenous material, is the most efficient with regard both to the growth of the strain ($\mu$max 0.47 h-1) and the biosynthesis of the polysaccharide (viscosity approaches 400 cps at end of cultivation).

Various culture media were studied, including those having the following composition:

| RCVs | |
|---|---|
| Glucose | 20 g |
| Yeast extract | 1.72 g |
| Buffer solution (2) | 15 ml |

-continued

| | |
|---|---|
| Mineral solution (1) | 50 ml |
| Osmosed water | qs ad 1 liter |

DSM

| | |
|---|---|
| Glucose | 20 g |
| Corn steep | 5 g |
| NaNO3 | 2 g |
| $K_2HPO_4$ | 1 g |
| $MgSO_4, 7H_2O$ | 1.5 g |
| Solution E (3) | 2.5 ml |
| Osmosed water | qs ad 1 liter |

Composition of the mineral solutions (1), buffer (2) and E (3)

(1) Mineral solution

| | |
|---|---|
| EDTA (tritriplex II) | 0.4 g |
| $MgSO_4.7H_2O$ | 2 g |
| $CaCl_2.2H_2O$ | 2 g |
| $FeSO_4.7H_2O$ | 0.44 g |
| Elements in solution | 20 ml |
| Osmosed water | qs ad 1 liter |

Elements in solution

| | |
|---|---|
| $ZnSO_4.7H_2O$ | 430 mg |
| $MnSO_4.7H_2O$ | 1300 mg |
| $Na_2MoO_4.2H_2O$ | 750 mg |
| $H_3BO_3$ | 2800 mg |
| $CuSO_4.5H_2O$ | 22.5 mg |
| $CoSO_4.7H_2O$ | 70 mg |
| Osmosed water | qs ad 1 liter |

(2) Buffer solution

| | |
|---|---|
| $KH_2PO_4$ | 40 g |
| $K_2HPO_4$ | 60 g |
| Osmosed water | qs ad 1 liter |

(3) Solution E

| | |
|---|---|
| $CaCl_2.2H_2O$ | 3 g |
| FeIII nitrate | 1 g |
| $MnSO_4$ | 0.2 g |
| $ZnCl_2$ | 0.1 g |
| $CuSO_4.5H_2O$ | 0.025 g |
| $Na_2B_4O_7.10H_2O$ | 0.02 g |
| $CaCl_2$ | 0.004 g |
| $Na_2MoO_4.2H_2O$ | 0.01 g |
| Osmosed water | qs ad 1 liter |

NA

| | |
|---|---|
| Meat extract | 3 g |
| Peptone | 5 g |
| Osmosed water | qs ad 1 liter |

The results are shown in Table III:

TABLE III

| Medium | C/N ratio | OD at 600 nm max | $\mu$max (h-1) | Final viscosity at 26s-1, 20° C. (cps) |
|---|---|---|---|---|
| RCVs | 50 | 2.70 | 0.28 | 227 |
| DSM+ | 8 | 6.20 | 0.38 | 254 |
| NA | 0.1 | 1.91 | 0.35 | 17 |

As Table III shows, media rich in nitrogen and low in carbon (low C/N) such as NA medium promote the growth of the strain but prevent production of polysaccharides. On the other hand RCV and DSM media, which are rich in nitrogenous and carbonaceous substrates, are the best compromise and give good growth of the strain combined with synthesis of polysaccharides. These tests have also shown that growth of the strain can be dissociated from production of polysaccharides.

An improved preculture medium for growth of the strain was thus chosen, the composition for a 7.5% inoculum being as follows:

Opt2_ns

| | |
|---|---|
| Glucose (sterilised separately) | 20 g |
| Yeast extract | 2.5 g |
| Ammonium sulphate | 1 g |
| Mineral solution (1) | 70 ml |
| Buffer solution (2) | 20 ml |
| Osmosed water | qs ad 1 liter |
| Inoculum | 7.5% |

Similarly an improved medium for production of exopoly-saccharide was developed in order to maximise the yield of polymer. The composition, hereinafter called MP1, was thus defined as the most efficient.

MP1

| | |
|---|---|
| Glucose | 20 g |
| Yeast extract | 1.7 g |
| Mineral solution (1) | 70 ml |
| Osmosed water | qs ad 1 liter |

Table IV shows the results for growth and production using RCVs medium alone (reference) or the two optimised media hereinbefore—Opt2_ns and MP1.

TABLE IV

| | | REFERENCE CYCLE | IMPROVED CYCLE |
|---|---|---|---|
| PRE-CULTURE | Medium | RCVs | Opt2_ns |
| | % inoculum | 0.22 | 0.37 |
| | Final corrected OD at 600 nm | 0.6 | 1.6 |
| | Duration | 20 hours | 15 hours |
| PRO-DUCTION | Medium | RCVs | MP1 |
| | $\mu$max (h-1) | 0.28 | 0.29 |
| | Final corrected OD at 600 nm | 8.9 | 9.2 |
| | Final concentration of EPS | 10.1 g/l | 10.2 g/l |
| | dS/dt Consumption of glucose | 0.25 g/l.h | 0.30 g/l.h |
| | dP/dt Yield of EPS (Production phase) | 0.27 g/l.h | 0.36 g/l.h |
| | Viscosity at 25° C. | 1500 cps at $26s^{-1}$ | 1560 cps at 26s#1 |
| | Duration of fermentation | 73 hours | 63 hours |
| | Duration of production phase | 38 hours | 28 hours |
| | Total duration of cycle | 93 hours | 78 hours |

Two methods can be used for recovering the polysaccharide produced by the strain by fermentation as explained hereinbefore.

In a first method, the crude broth is subjected to precipitation with ethanol then to drying in vacuo to obtain a dry product containing the crude polysaccharide. The product, which is redissolved at 1%, has viscosifying properties. This solution, when heated to a temperature between 70 and 95° C. (preferably between 85 and 95° C.) has the same gel-forming properties as the solution prepared from the purified polysaccharide as obtained in the second method hereinafter.

In the second method the fermentation broth is drawn off and diluted to between 1 and 1/20, preferably between 1 and 1/10. The solution is then brought to a temperature between 70 and 95° C.; preferably the heat treatment is carried out between 85 and 95° C. This is because heat-treatment at 90° C. liquefies the fermentation broth, even after cooling to ambient temperature. In the case of treatment at 90° C. for about an hour, the gelation or cooling temperature is below 20° C.

If the heat-treatment is carried out at a temperature below 90° C., the result after cooling is a product which is more viscous than the initial broth.

It is clear therefore that heat treatment of this kind can facilitate separation of cells from polymers (inter alia by centrifuging).

The product after heat treatment is centrifuged for example at 13000 g or subjected to tangential filtration.

The supernatant thus obtained is subjected to frontal filtration at 0.2 μm on a plate filter. Frontal filtration gives an extremely pure filtrate having practically zero optical densities (ODs) at 600 nm (Table V).

TABLE V

| Cut-off threshold (μm) | OD of the filtrate at 600 nm |
| --- | --- |
| 0.8 | 0.02 |
| 0.45 | 0.005 |
| 0.8 then 0.45 | 0.007 |
| 0.8 then 0.22 | 0.003 |
| 0.45 then 0.22 | 0.002 |

Pressure applied: $2.10^5$ pascals

The recovered filtrate,is treated in known manner; it is concentrated, precipitated with ethanol then dried in vacuo to obtain a dry product comprising a purified exopolysaccharide.

As stated hereinbefore, the exopolysaccharide is novel, both in its nature and its properties.

The structure of the resulting polysaccharide was determined via the RMN spectrum as shown in FIGS. 1 and 2. This showed that the repeat unit, which has a side chain, is made up mainly of seven sugars, that is:

6 neutral sugars including glucose and galactose and 1 acid sugar.

The presence of pyruvate and acetate substituents was also shown. Pyruvate fillers and acid sugars give this polysaccharide the properties of a polyelectrolyte. During use, at concentrations of polysaccharide in accordance with the invention above 2 g/l, the solutions thereof are converted into gel. The gel is obtained by dissolving in water or in any saline aqueous solution. The polysaccharide solution in accordance with the invention dissolves more easily if heated, preferably to above 60° C.

The polysaccharide in accordance with the invention in 1% solution is perfectly clear, "crystal grade", which gives it a privileged position over known products such as those sold under the trade mark AMIGEL by Messrs A. MULLER or under the name CURDLAN by Messrs TAKEDA, or xanthanes sold by Messrs KELCO or sodium alginates as proposed by Messrs SANOFI (see Table VI hereinafter).

TABLE VI

| Product | Coloration OD at 420 nm | Turbidity OD at 600 nm | OD at 860 nm |
| --- | --- | --- | --- |
| Gel in accordance with the invention | 0.060 | 0.031 | 0.020 |
| Amigel | 1.200 | 0.958 | 0.742 |
| Curdlan | 1.232 | 1.601 | 1.629 |
| Xanthane LT | 0.302 | 0.187 | 0.124 |
| Sodium alginates | 0.216 | 0.133 | 0.091 |

The polysaccharide in accordance with the invention also dissolves more quickly than the known substances (Table VII).

TABLE VII

| Product | Type of powder | Time to redissolve |
| --- | --- | --- |
| Gel in accordance with the invention | Non-wettable | A few minutes |
| Amigel | Wettable | A few hours |
| Xanthane | Not wettable | A few tens of minutes |

A study of the mechanical properties of the polysaccharide gels in accordance with the invention has shown that this gel is very elastic: FIG. 3 shows the effect of frequency (Hz) on the elastic modulus G' and loss modulus G" and on the complex viscosity n* of a polysaccharide gel in accordance with the invention (the polysaccharide concentration is 0.10 g/l and the NaCl concentration is 0.1 M).

The effect of the ionic strength on the elastic modulus of gels containing 1% (wt/wt) polysaccharide was also studied: FIG. 4 shows the effect of the concentration of salt (NaCl) on the modulus of elasticity, measured at the frequency of 0.13 Hz, of a polysaccharide gel in accordance with the invention at a concentration of 10 g/l.

As can be seen, at a concentration of NaCl of 0.04 M or above, the resulting elastic gel has characteristics which are practically unaffected by the concentration of salt, at least up to 0.4 M. Very similar moduli are obtained in the presence of $CaCl_2$. The gels formed are thermo-reversible in the case of heat treatment below 90° C. FIG. 5 shows the influence of temperature on the elastic modulus G' and loss modulus G" and on the complex viscosity n* of a polysaccharide gel in accordance with the invention (the polysaccharide concentration being 10 g/l and the concentration of NaCl being 0.10 M).

The results however depend on the temperature and duration of treatment, with the risk of destroying the gel at excessive temperatures and/or treatment times. The melting-point of the gel is very little affected by the ionic strength or the nature of the ions (such as $Na^+$ or $Ca^{2+}$).

These Theological properties in a salty medium are extremely important, since they offer the prospect of applications to numerous industries associated with the three natural salty media: that is

| taste (approx. 1.5 g salt/L): | food |
| --- | --- |
| physiological salt | agriculture, cosmetics, |

| | |
|---|---|
| solution (about 7.5 g salt/L): | pharmacy etc. |
| the marine environment (about 25 g salt/L): | oil industry, cosmetics (marine range), etc. |

In order to illustrate these different sectors, sample applications and formulations of the polysaccharide in accordance with the invention are given hereinafter, without however being limitative.

1. Cosmetics

The polysaccharide in accordance with the invention can be applied as:

- a moisturising agent, alone or mixed with known moisturising agents such as hyaluronic acid in creams and lotions,
- a thickener or texturing agent in lotions, tonics and creams (white cosmetic),
- a suspension agent and texturing agent in exfoliant gels or solar filters,
- a gelling agent in hair gels, before and after-shave gels and bath gels (shampoos and foam baths).

The following are a few kinds of applications:"

Moisturising Cream (% wt/wt dry substance)

| | |
|---|---|
| Emulsifier | 4.0% |
| Preservative | 0.5% |
| Glycerol | 5% |
| Polysaccharide according to the invention | 0.25% |
| NaCl | 0.5% |
| Water qs ad | 100% |

In this application, the polysaccharide in accordance with the invention provides specially advantageous products as compared with certain competing products, as regards lubricating quality, ease of spreading and coolness. Considerable effects on the reduction of its tendency to form strands, the stickiness, the film-forming effect, the brilliance of the skin and the fluidity have been observed as shown in FIG. 6.

Make-up Remover (% wt/wt dry substance)

| | |
|---|---|
| Sodium dodecyl-tetradecyl galacturonate | 0.5% |
| Sodium hyaluronate | 0.2% |
| Polysaccharide according to the invention | 0.4% |
| Blueberry water | 5.0% |
| Preservative | qs |
| Scent, dye | qs |
| Water qs ad | 100.0% |

Exfoliant Gel (% wt/wt dry substance)

| | |
|---|---|
| Polysaccharide according to the invention | 0.75% |
| NaCl | 0.5% |
| Carboxymethyl cellulose | 0.5% |
| Crushed apricot kernel | 2.0% |
| Preservative, dye, scent | qs |
| Water qs ad | 100.0% |

Bath Gel (% wt/wt dry substance)

| | |
|---|---|
| Sodium decyl-dodecyl galacturonate | 4.0% |
| Lauryl betaine | 3.0% |
| Laureth(2) sulphate | 3.0% |
| Acylate peptides (C12) | 2.0% |
| Ethoxylated capric-caprilic acid mono/oligoglyceride | 1.0% |
| Disodium lauryl sulphosuccinate | 1.0% |
| Polysaccharide according to the invention | 0.5% |
| NaCl | 0.25% |
| Preservative, scent, dye | qs |
| Water qs ad | 100.0% |

II—Detergents

The polysaccharide in accordance with the invention is of use as a

- texturing agent and suspension agent in scouring creams and gels
- a gelling agent in deodorising and disinfectant gels
- a texturing agent in washing-up liquids.

In the case of a scouring cream, one possible formulation is:

| | |
|---|---|
| Polysaccharide according to the invention | 1.0% |
| NaCl | 0.5% |
| Calcined aluminium silicate | 25.0% |
| Sodium lauryl sulphate | 5.0% |
| Caprylo-ampho-proprionate | 1.0% |
| Preservative, dye, scent | qs |
| Water qs ad | 100.0% |

III—Food

The polysaccharide in accordance with the invention is of use as:

- a texturing agent, gelling agent and suspension agent in milky desserts, vinaigrettes, sauces (mayonnaise or others), jellies and preserves, aspic jellies and terrines
- a texturing agent in diet drinks and confectionery.

The following is a sample formulation for cold chocolate flan (% wt/wt dry substance):

| | |
|---|---|
| UHT milk | 83.0% |
| Polysaccharide in accordance with the invention | 1.2% |
| NaCl | 0.1% |
| Sugar | 8.0% |
| Cocoa | 3.0% |
| Skimmed powdered milk | 2.0% |
| Vegetable Oil | 0.7% |
| Vanilla flavour | qs |
| Eggs | 2.0% |

IV—Fermentation

In this sector, the polysaccharide in accordance with the invention gives a gel texture to semi-solid gelose culture medium. The following is a sample formulation for a semi-solid gelose medium in % wt/wt of dry substance:

| | |
|---|---|
| Peptones | 1% |
| Glucose | 0.5% |
| NaCl | 0.5% |
| Polysaccharide in accordance with the invention | 0.75% |
| Water qs ad | 100% |

V—Agriculture

In agriculture, the polysaccharide in accordance with the invention is of use as a soil aggregation agent, a water-retaining agent, helping to maintain the hydric potential of soil and an anti-drought agent and a seed-coating agent.

For example, inoculation of sunflower seeds with the strain Rhizobium resulted in strong colonisation of the roots, whether or not the ground had previously been sterilised (90% and 10% of the total microflora respectively). Inoculation results in an increase in the mass of soil adhering to the roots (plus 50%) and a modification of the porosity of the rhizospheric soil (increase in macroporosity). These results indicate that the exopolysaccharide produced by the strain YAS 34 is of help in bringing together soil aggregates (a "sticking" effect) and thus increases the frequency of the pores for transferring water to the plant and also retains water in a gelled polysaccharide phase.

To confirm the water-retaining power of the polymer, mixtures of soil plus 1% purified polysaccharide were prepared. The results showed that at pF 2.5 (capacity in the field), the polysaccharide increases water retention of the soil by 50% and likewise, if 1% polymer is added, it is necessary to supply twice as much energy to dehydrate the soil.

Figure 1:
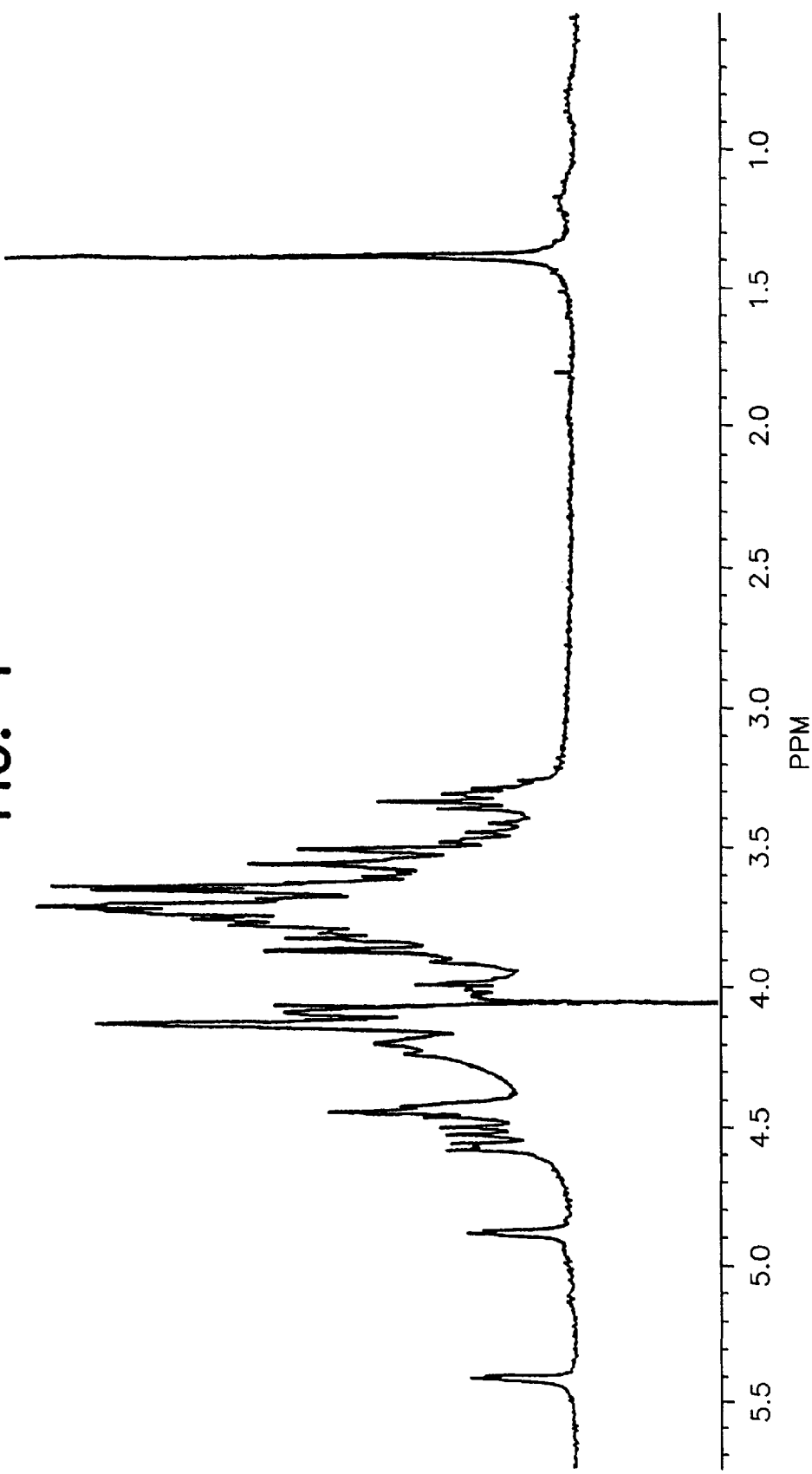
FIG. 1—Deacetylated polysaccharide in accordance with the invention. RMN'H spectrum (300 MHz), solution in $D_2O$, T=358° K FIG. 2—The Polysaccharide in accordance with the invention. $RMN^1H$ spectrum (300 MHz), solution in $D_2O$, T=358° K FIG. 3—Influence of frequency on the elastic modulus (G') and the loss modulus (G") and on the complex viscosity n* of the gelled polysaccharide in accordance with the invention. Polysaccharide concentration 10 g/L, NaCl concentration 0.1 M.
Figure 2:
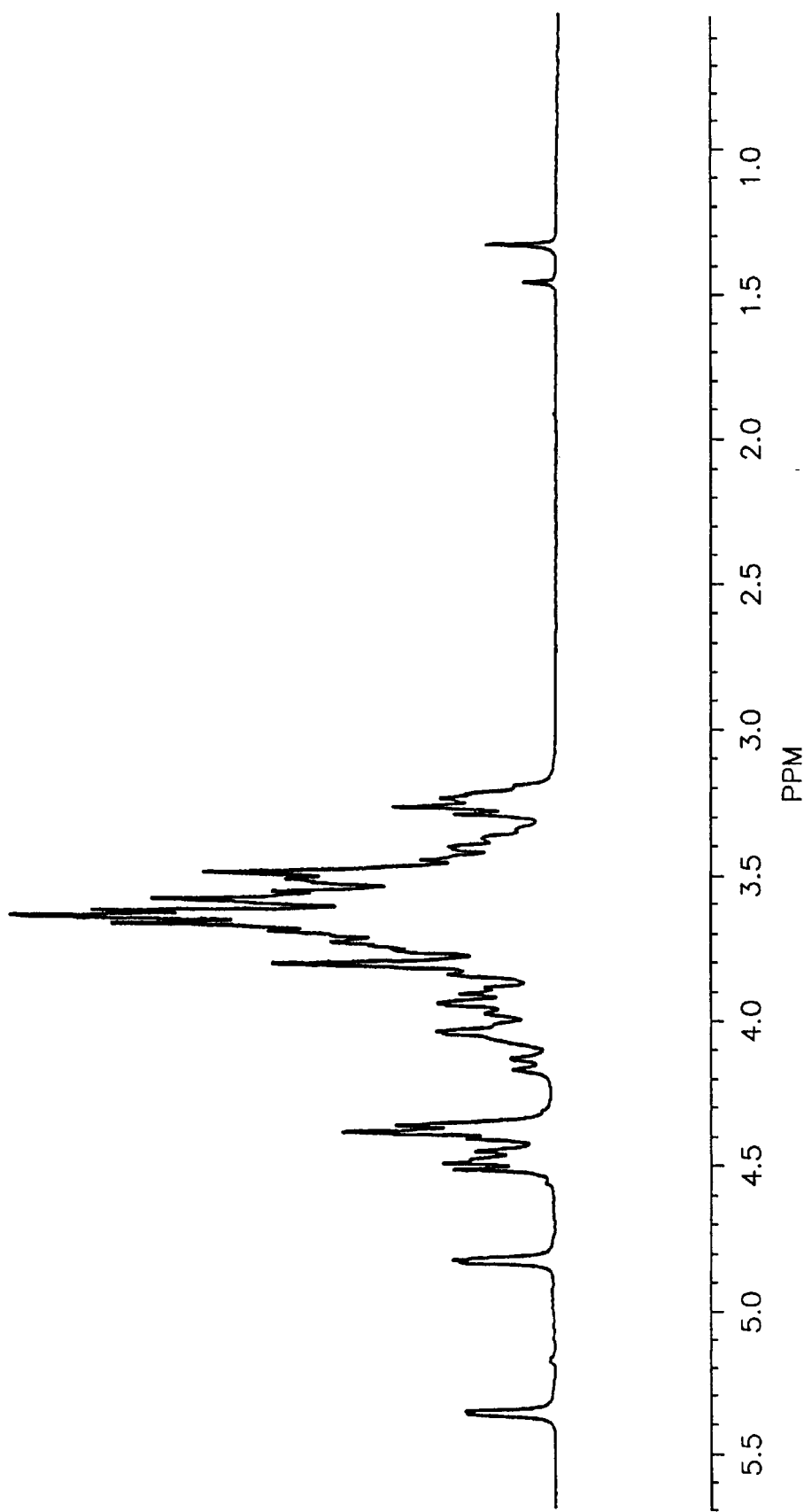
Figure 3:
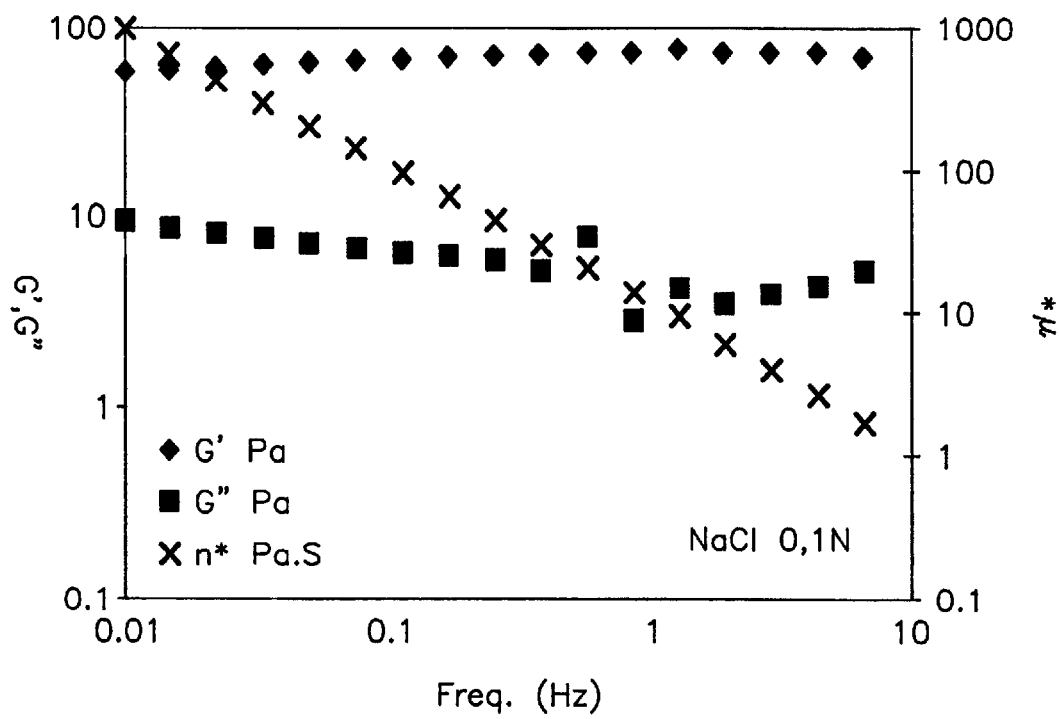
Figure 4:
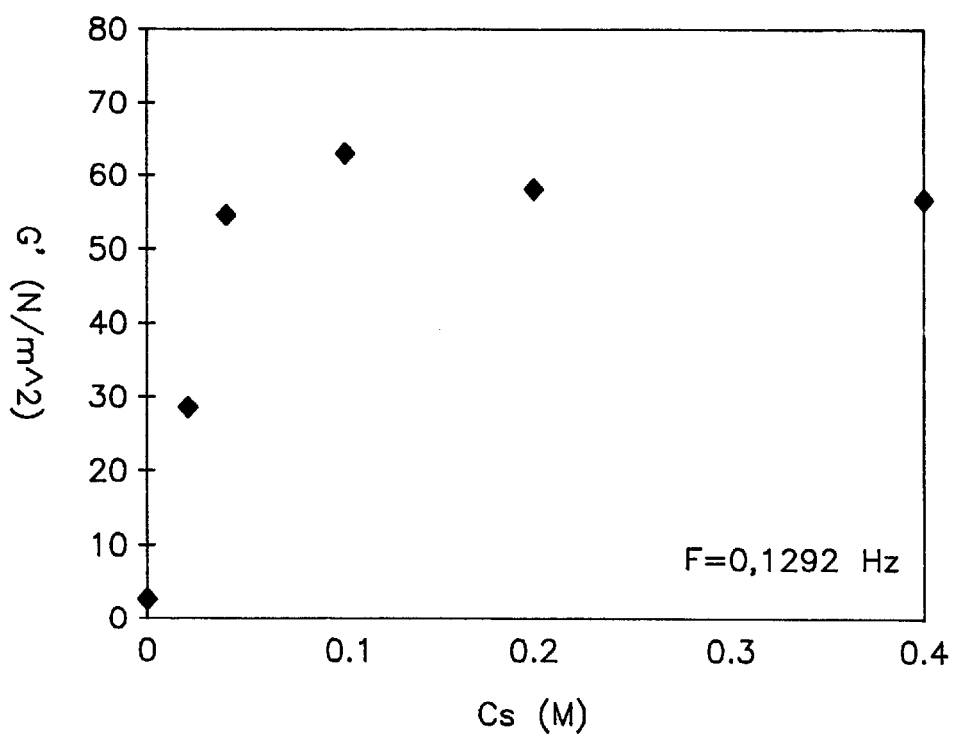
FIG. 4—Influence of the concentration of salt (NaCl) on the elastic modulus, measured at the frequency 0.13 Hz, of a polysaccharide gel in accordance with the invention at the concentration of 10 g/l.
Figure 5:
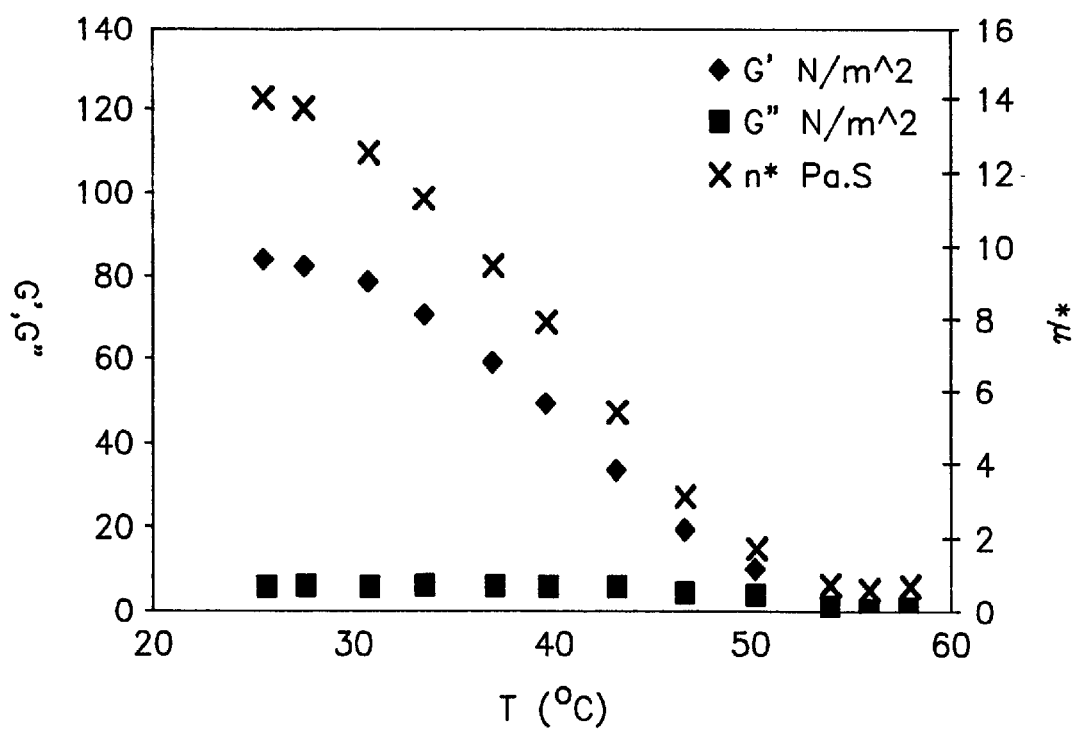
FIG. 5—Influence of the temperature on the elastic modulus (G') and the loss modulus (G") and on the complex viscosity n* of the polysaccharide gel in accordance with the invention. Polysaccharide concentration 10 g/L, NaCl concentration 0.1 M.
Figure 6:
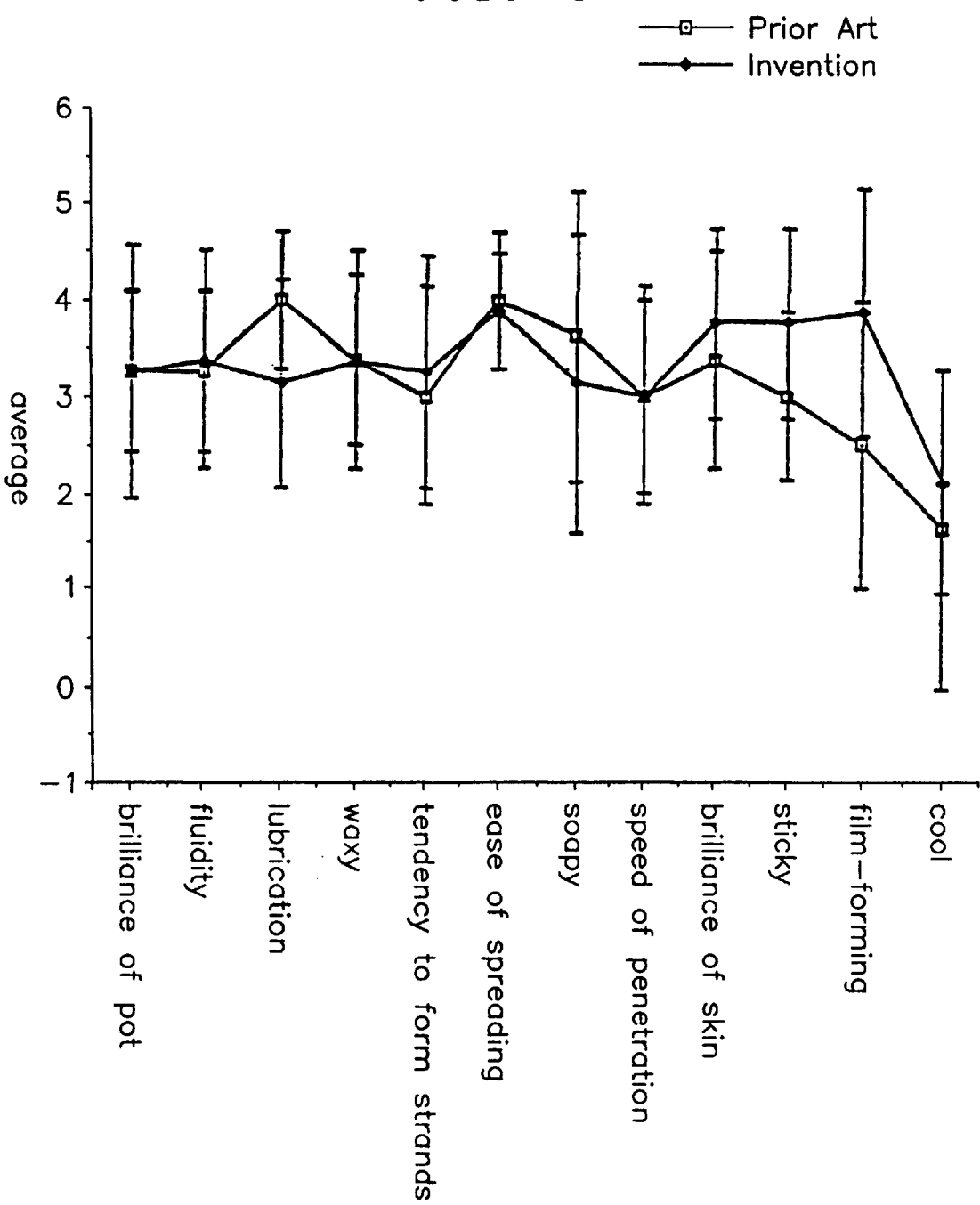
FIG. 6—Sensory test for comparing a prior-art moisturising cream formulation (prior art) with a moisturising cream formulation in accordance with the invention (invention) comprising 0.25% of a polysaccharide in accordance with the invention and sodium chloride.

Finally the polysaccharide in accordance with the invention is also of use as a moisturising agent, a thickener or a suspension agent in paints.

What is claimed is:

1. A polysaccharide having a repeating unit which has a side chain and consists of six neutral sugars, including glucose and galactose, and an acid sugar, the polysaccharide being such that an aqueous solution containing 0.2% or more by weight thereof forms an elastic, transparent gel.

2. A polysaccharide according to claim 1, which is readily water soluble at a temperature in excess of 60° C.

3. A polysaccharide according to claim 1, which, in solution in water at a concentration of 0.2% by weight and in the presence of salt, forms an elastic, transparent, suspended gel.

4. An isolated micro-organism capable of synthesising a polysaccharide according to claim 1 which is a Rhizobium deposited under number 1-1809 at the CNCM.

5. A method of producing a polysaccharide according to claim 1, which comprises the following steps:

a) cultivating a micro-organism on a medium rich in glucose and in nitrogenous substance, b) recovering the fermentation broth, and c) directly obtaining the polysaccharide in crude form by precipitation.

6. A method according to claim 5, which comprises processing the fermentation broth from step b) as follows:

d) heat-treating the broth after dilution at a temperature between 70 and 95° C., e) centrifuging, f) filtering the supernatant from step d), and g) processing resulting filtrate to obtain the polysaccharide in dry form.

7. A method according to claim 5, in step a) of which two culture media, a precultivation medium and a production medium, are used.

8. A method according to claim 7, wherein the "precultivation" medium has the following composition:

| | |
|---|---|
| Glucose (sterilised separately) | 20 g |
| Yeast extract | 2.5 g |
| Ammonium sulphate | 1 g |
| Mineral solution (1) | 70 ml |
| Buffer solution (2) | 20 ml |
| Osmosed water | qs ad 1 liter |
| Inoculum | 7.5%. |

9. A method according to claim 7, wherein the "production" medium has the following composition:

| | |
|---|---|
| Glucose | 20 g |
| Yeast extract | 1.7 g |
| Mineral solution (1) | 70 ml |
| Osmosed water | qs ad 1 liter. |

10. A method according to claim 5, characterised in that micro-organism is a Rhizobium deposited under No. 1-1809 at the CNCM.

11. A cosmetic composition comprising a polysaccharide according to claim 1 as a moisturizing agent, a thickener, a gelling agent or a suspension agent.

12. A detergent composition comprising a polysaccharide according to claim 1 as a gelling agent or as a suspension agent.

13. A food product comprising a polysaccharide according to claim 1 as a texturising agent or a suspension agent.

14. A gelose fermentation medium comprising a polysaccharide according to claim 1 as a gelling agent.

15. An agricultural composition comprising a soil aggregation agent, a water-retaining agent or a seed coating agent wherein the agent is a polysaccharide according to claim 1.

16. A paint composition comprising a texturising agent, a thickening agent or a suspension agent, wherein the agent is a polysaccharide according to claim 1.

17. A composition comprising a member selected from the group consisting of a thickening agent, a gelling agent, a suspension agent, a texturizing agent and a water-retaining agent, wherein the member is a polysaccharide according to claim 3.

* * * * *